(12) United States Patent
Asenjo De Leuze et al.

(10) Patent No.: US 11,261,472 B2
(45) Date of Patent: Mar. 1, 2022

(54) PEPTIDE SEQUENCE OF A GUIDE PROTEIN FOR THE PRODUCTION OF A PEPTIDE OF INTEREST, AN EXPRESSION VECTOR, A HOST CELL, AND A METHOD FOR THE PRODUCTION OF A PEPTIDE OF INTEREST

(71) Applicant: UNIVERSIDAD DE CHILE, Santiago (CL)

(72) Inventors: Juan Alfonso Asenjo De Leuze, Santiago (CL); Barbara Anne Andrews Farrow, Santiago (CL); Vida Rodriguez Gallardo, Santiago (CL)

(73) Assignee: UNIVERSIDAD DE CHILE, Santiago (CL)

( * ) Notice: Subject to any disclaimer, the term of this patent is extended or adjusted under 35 U.S.C. 154(b) by 118 days.

(21) Appl. No.: 16/474,805

(22) PCT Filed: Dec. 28, 2017

(86) PCT No.: PCT/IB2017/058480
§ 371 (c)(1),
(2) Date: Sep. 6, 2019

(87) PCT Pub. No.: WO2018/122777
PCT Pub. Date: Jul. 5, 2018

(65) Prior Publication Data
US 2020/0385774 A1 Dec. 10, 2020

(30) Foreign Application Priority Data
Dec. 30, 2016 (CL) .................................. 201603427

(51) Int. Cl.
*C12P 21/02* (2006.01)
*C07K 14/46* (2006.01)
*C12N 15/62* (2006.01)
*C12N 15/67* (2006.01)

(52) U.S. Cl.
CPC .............. *C12P 21/02* (2013.01); *C07K 14/46* (2013.01); *C12N 15/62* (2013.01); *C12N 15/67* (2013.01)

(58) Field of Classification Search
None
See application file for complete search history.

(56) References Cited

U.S. PATENT DOCUMENTS

| 8,796,431 B2 | 8/2014 | Stowell et al. |
| 2003/0096263 A1* | 5/2003 | Oliveira ............... G01N 33/574 435/6.16 |
| 2010/0234568 A1 | 9/2010 | Decarolis et al. |
| 2015/0051374 A1 | 2/2015 | Liu et al. |
| 2016/0208304 A1 | 7/2016 | Stowell et al. |

FOREIGN PATENT DOCUMENTS

WO 9617942 A1 6/1996

OTHER PUBLICATIONS

"Chain A, A-Spectrin Sh3 Domain A11v, V23I, M25i, V53i, V58I Mutant", <https://www.ncbi.nlm.nih.gov/protein/1 E6G_A>, 2012, 2 Pages.
Rodriguez et al., "Design and implementation of a high yield production system for recombinant expression of peptides", Microbial Cell Factories, 2014, vol. 13:65, pp. 1-10.
Yadav et al., "An insight into fusion technology aiding efficient recombinant protein production for functional proteomics", Archives of Biochemistry and Biophysics, 2016, vol. 612, pp. 57-77.
International Search Report for Corresponding International Application No. PCT/IB2017/058480, (4 Pages) (dated Apr. 12, 2018).

* cited by examiner

*Primary Examiner* — Suzanne M Noakes
(74) *Attorney, Agent, or Firm* — Lucas & Mercanti, LLP

(57) ABSTRACT

A peptide sequence of a guide protein for the production of a peptide of interest; a peptide sequence that has a similarity of at least 90% to SEQ. ID. NO 1; a nucleotide sequence encoding the guide protein; an expression vector comprising the nucleotide sequence; a host cell that expresses a fusion protein comprising a peptide of interest; a method of production of a peptide of interest, comprising the steps of A) constructing an expression vector; B) inserting the expression vector into a host cell; C) expressing the fusion protein, culturing the host cell in a culture medium; D) recovering the accumulated fusion protein in the host cell; E) cleaving the fusion protein; F) purifying the peptide of interest.

20 Claims, 4 Drawing Sheets

Specification includes a Sequence Listing.

PEPTIDE SEQUENCE OF A GUIDE PROTEIN FOR THE PRODUCTION OF A PEPTIDE OF INTEREST, AN EXPRESSION VECTOR, A HOST CELL, AND A METHOD FOR THE PRODUCTION OF A PEPTIDE OF INTEREST

CROSS REFERENCE TO RELATED APPLICATION

This Application is a 371 of PCT/IB2017/058480 filed on Dec. 28, 2017, which claims the benefit of Chilean Patent Application No. 201603427, filed Dec. 30, 2016, which is incorporated herein by reference.

FIELD OF THE INVENTION

The present application describes a peptide sequence of a guide protein derived from the SH3 domain of the protein spectrin, hereinafter called SSD guide protein, for the production of peptides of interest in the form of a fusion protein.

STATE OF ART

The study of peptides at the therapeutic level and as a diagnostic method has generated great interest in the pharmaceutical industry due to its low toxicity, high specificity and high biological activity, (Vlieghe P et al, Drug Discov Today 2010, 15-40, 56); as well as agricultural use, Hughes S R et al., 2012, Pharmaceuticals 5 (10): 1054-1063; and as antimicrobial agent, Yifeng Li, 2011, Protein Expression and Purification 80: 260-267.

Short peptides, composed of less than 20 amino acids, are commonly produced by chemical synthesis, with the sequential addition of each amino acid (aa). This method is, in general, not suitable for the production of peptides of more than 30 amino acids, since its yield decreases with the increase in the size of the peptide. In addition, it uses an excess of reagents to favor the reaction to the products, which increases costs and generates a lot of waste, some of them toxic to the environment such as acids, limiting its scalability.

The recombinant production of peptides has many advantages over chemical synthesis, including potentially higher yield, lower cost, better scalability and less residual contamination. However, although any polypeptide chain can be theoretically expressed in any microbial system, the cytoplasmic expression of peptides usually generates problems in the stability of the expressed peptide, resulting in a diminishing yield. In fact, peptides expressed in a host cell can be rapidly degraded by endogenous proteases and assimilated by the host cell.

To overcome this problem, peptides can be expressed and fused to guide proteins, which can additionally direct the peptides to specific subcellular compartments or inclusion bodies with the aim of achieving a high expression yield and avoiding degradation by proteases. For this reason, guide proteins are particularly a good alternative for the synthesis of peptides between 30 and 50 aa, for which the chemical and traditional recombinant synthesis are not cost-efficient options.

Currently, there are some commercial guide proteins for the production of peptides, such as intein-CBD (Chitin binding domain) from New England Biolabs and KSI (Ketoesteroid Isomerase) from Novagen, among others. Some of the drawbacks of using these guide proteins are the low yields obtained, additional difficulty for eliminating these residues (release of unwanted peptides, generation of precipitates), usually under extreme chemical conditions that result in undesired chemical modifications in the peptide of interest. This is why new high-throughput recombinant expression techniques for the production of peptides, through the use of new guide proteins and with a downstream method of simplified purification, must be developed.

Below there are relevant documents of the state of the art of the technique in question.

The publication "A FUSION PROTEIN SYSTEM FOR THE RECOMBINANT PRODUCTION OF SHORT DISULFIDE-CONTAINING PEPTIDES", Fairlie, W. Douglas, et al. Protein expression and purification, 2002, vol. 26, no 1, p. 171-178, describes a recombinant fusion protein system for the production, oxidation and purification of short peptides containing a single disulfide bridge. Peptides are expressed in Escherichia coli fused to a mutant protein of the N-terminal SH2 domain of intracellular phosphatase, SH2-P. This small protein domain confers several important properties that facilitate the production of disulfide-containing peptides:

(i) is expressed at high levels in E. coli; (ii) can be purified using a Hexahistidine and reverse phase HPLC; (iii) does not contain endogenous cysteine residues, allowing the formation of a disulfide intrapeptide while still bound to the guide protein; (iv) it is highly soluble in native solutions, facilitating the production of highly hydrophobic peptides and the direct use of fusion products in biochemical assays; (v) contains a single methionine residue at the junction of the peptide and the guide protein to facilitate cleavage of the peptide by treatment with cyanogen bromide (CNBr). However, this document does not mention the use of a protein derived from spectrin.

The U.S. Pat. No. 8,796,431, claims a method for the production of peptides of interest. The method consists of expressing a heterologous fusion peptide in a genetically modified cell, wherein the fusion peptide comprises an affinity tag, a cleavage sequence and the peptide of interest, wherein the cleavage sequence is tryptophan (Trp) and the cleavage reaction is performed in the presence of N-chlorosuccinide, while the fusion peptide is bound to the affinity material, releasing the peptide of interest. However, this document does not mention the use of a protein derived from spectrin.

The publication "DESIGN AND IMPLEMENTATION OF A HIGH YIELD PRODUCTION SYSTEM FOR RECOMBINANT EXPRESSION OF PEPTIDES". Rodriguez et al. Biomed Central. Microbial Cell Factories 2014, 13:65, 2014, describes the expression of peptides fused to the ketosteroid isomerase protein (KSI) in a form that can be subsequently separated and obtained with their original sequence by cutting with thrombin. With this system, a productivity of 30 mg of peptide per gram of dry cell weight was obtained. However, this document does not mention the use of a protein derived from spectrin.

The US Patent 20150051374, claims a method for producing recombinant peptides containing between 10 and 200 amino acids using new guide proteins derived from the green fluorescent protein and its mutants. However, this document does not mention the use of a protein derived from spectrin.

The document WO 1996017942, claims a method for the isolation and/or purification of a recombinant peptide employing a fusion protein construct that includes a carbonic anhydrase and a variable fused polypeptide. The method includes the precipitation of the fusion protein or a fragment of the fusion protein that includes carbonic anhydrase. It also includes the method for expressing the fusion protein as part of the inclusion bodies. However, this document does not mention the use of a protein derived from spectrin.

This way, none of the reviewed documents from the state of art describes the use of a guide protein derived from spectrin for the expression of a peptide of interest. The present application thus describes a guide protein derived from spectrin (SSD), used in the construction of an expression vector, which is inserted into a host cell, allowing the expression of a peptide of interest in a concentration close to 130 mg of peptide of interest for each gram of dry cell.

DESCRIPTION OF THE INVENTION

Figure 1:
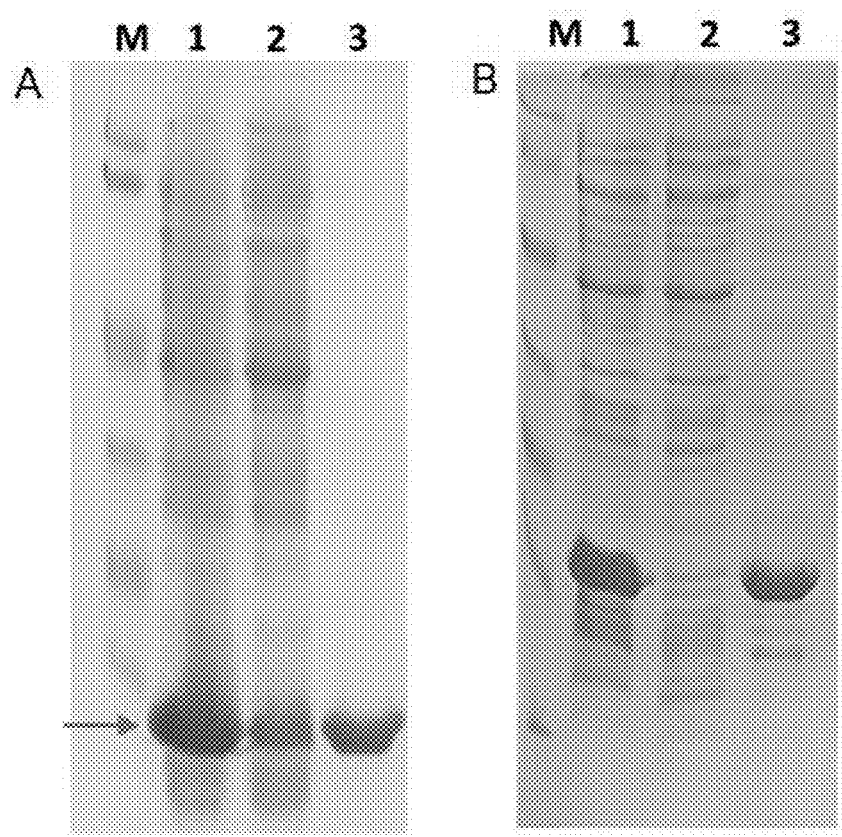
FIG. 1: Comparison of expression of the fusion protein using SSD guide protein (FIG. 1A), vs using KSI guide protein (FIG. 1B) for the production of the peptide of interest p53pAnt. In this figure it is shown a comparison of the SDS-PAGE analysis of the intracellular protein 1: total protein, 2: soluble protein, 3: insoluble protein. In column 1, it is observed that when using the SSD guide protein, a higher total fusion protein productivity is obtained with respect to the productivity obtained when using the KSI guide protein; in column 2, it is observed that with the SSD guide protein, fusion protein is obtained in soluble form, whereas with KSI it is not obtained; In column 3 it is observed that in the SSD case the insoluble fusion protein is in a higher degree of purity than when using the KSI guide protein, since no contaminating band is observed.

The present application refers to a peptide sequence, according to SEQ ID NO: 1, of a guide protein, here called SSD guide protein, which is used for the recombinant production of peptides of interest, included in a recombinant fusion protein, as well as the nucleotide sequence SEQ ID NO: 2, which encodes for said SSD guide protein.

The present application also discloses an expression vector comprising said sequence encoding said SSD guide protein, and a sequence encoding at least one peptide of interest. This expression vector is used for the recombinant production of a fusion protein.

The present application also describes a host cell transformed with said expression vector. This host cell, when cultured in the form of batch culture, semi-continuous culture, or continuous culture, expresses the fusion protein comprising the SSD guide protein, and the peptide of interest.

The present application also describes a method of production of recombinant peptides of interest. Said method comprises the construction of an expression vector for the recombinant production of a fusion protein. Said fusion protein comprises the SSD guide protein, and at least one copy of a peptide of interest. Said vector is introduced into a host cell, which expresses the fusion protein. The fusion protein produced further comprises a cleavage site between the sequences of the SSD guide protein and the peptide of interest, and a purification tag to facilitate the recovery of the recombinant protein.

This method includes the stages of
A) constructing expression vector,
B) inserting expression vector into host cell,
C) expressing the fusion protein,
D) recovering the fusion protein,
E) cleaving the fusion protein,
F) purifying the peptide of interest.
These stages are described in detail below:
A) Constructing Expression Vector.
Constructing an expression vector, which includes:
  a nucleotide sequence coding for the SSD guide protein of sequence SEQ ID NO: 1, or a nucleotide sequence coding for a guide protein with a similarity of at least 90% with respect to SEQ ID NO: 1,
  at least one sequence that encodes a peptide of interest,
  a sequence encoding a cleavage site, with which it is then possible to separate the peptide of interest from the rest of the protein, wherein the cleavage site is preferably a recognition site for the protease thrombin, and
  a sequence encoding a purification tag, with which it is then possible to facilitate the purification of the fusion protein, wherein the purification tag is preferably a polyhistidine tag.
B) Inserting Expression Vector into a Host Cell.
Introduce the expression vector constructed in step A, in a host cell, wherein the host cell is preferably selected from *Escherichia coli, Bacillus subtilis* or *Saccharomyces cerevisiae*.
C) Expressing the Fusion Protein.

This step consists of culturing the transformed host cells of step B, in a culture medium for the expression of the fusion protein, wherein the culture medium comprises a nutritive medium, a selection marker, and an inducer. Preferably said nutrient medium is Luria Bertani (LB medium); said selection marker is ampicillin; and said inducer is isopropyl-β-D-1-thiogalactopyranoside (IPTG).

In this culture, the transformed host cells produce the fusion protein comprising the peptide of interest, and the SSD guide protein. This fusion protein is accumulated by the host cell preferably in inclusion bodies.

This stage of expression of the fusion protein is carried out in a temperature range between 20 and 40° C., preferably between 23 and 26° C., and for a time between 1 and 24 hours for batch cultures, or for an indefinite period for a continuous crop.

This preferred temperature range between 23 and 26° C. is different from the preferred ranges commonly used in the state of art, which are usually between 35 and 40° C., preferably at 37° C.

Figure 4:
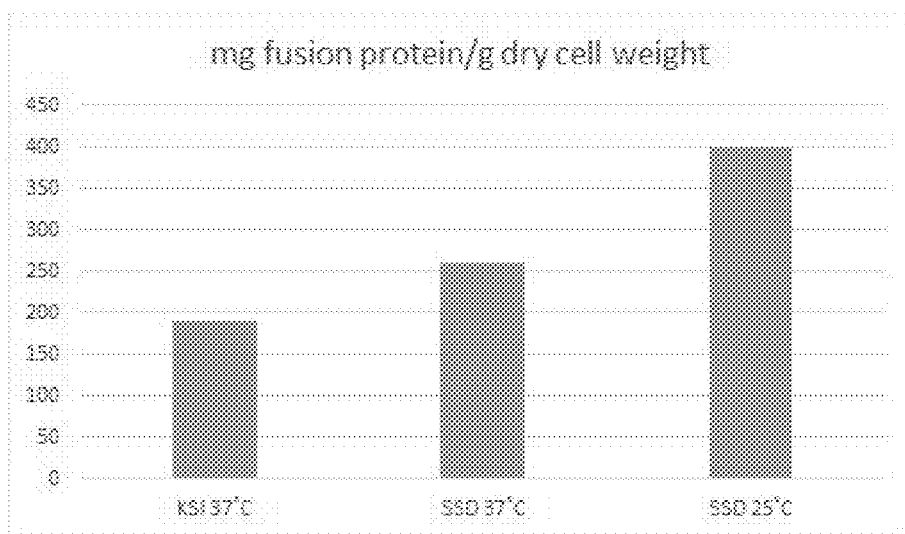
FIG. 4: Comparison of fusion protein productivity obtained using KSI guide protein at 37° C., SSD at 37° C., SSD at 25° C. It is observed that the productivity obtained with SSD guide protein at 37° C. is higher than that obtained with the guide protein of the state of art, also the productivity obtained by expressing at 25° C. is higher than that obtained at 37° C.

In this preferred temperature range between 23 and 26° C., the host cell obtains a productive result superior to that described in the state of art. (FIG. 4)

This superior productive result is not obtainable with any guide protein described in the state of art, besides the consequent reduction of the working temperature, generating an energy saving.

D) Recovering the Fusion Protein

Once the fusion protein containing the peptide of interest is produced and accumulated within the host cell, the present application describes a step of separating and purifying the fusion protein.

Said separation and purification step comprises lysing the host cell and then recovering the fusion protein in whole or in part using traditional separation and purification methods, such as centrifugation, precipitation and chromatography, wherein the chromatography method is preferably metal affinity chromatography.

E) Cleaving the Fusion Protein

The recovered fusion protein is solubilized in cleavage solution by at least one step of dialysis, dilution, retention in chromatography column, or precipitation and dissolution, and then to remove the SSD guide protein, it is processed by proteolytic methods, such as enzymatic proteolysis, chemical proteolysis by protease cleavage, chemical cleavage or metal-catalyzed cleavage, and where the cleavage solution is preferably a semi-denaturing solution and the proteolytic method is enzymatic proteolysis with thrombin.

F) Purifying the Peptide of Interest

Finally, the peptide of interest is recovered by chromatography and/or precipitation methods, preferably metal affinity chromatography, size exclusion, or reverse phase.

Among the technical advantages of the present application is that the method provides an improved result of fusion protein productivity when using a temperature range between 23 and 26° C., a value that is lower than that usually used between 35 and 40° C., saving energy (FIG. 4).

Figure 2:
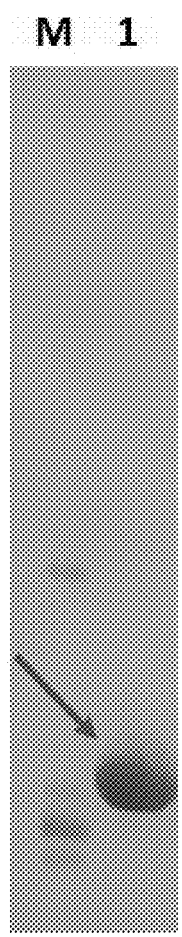
FIG. 2: SDS-PAGE analysis of the purified fusion protein from total protein in a single chromatography step. 1: Purified fusion protein.
Figure 3:
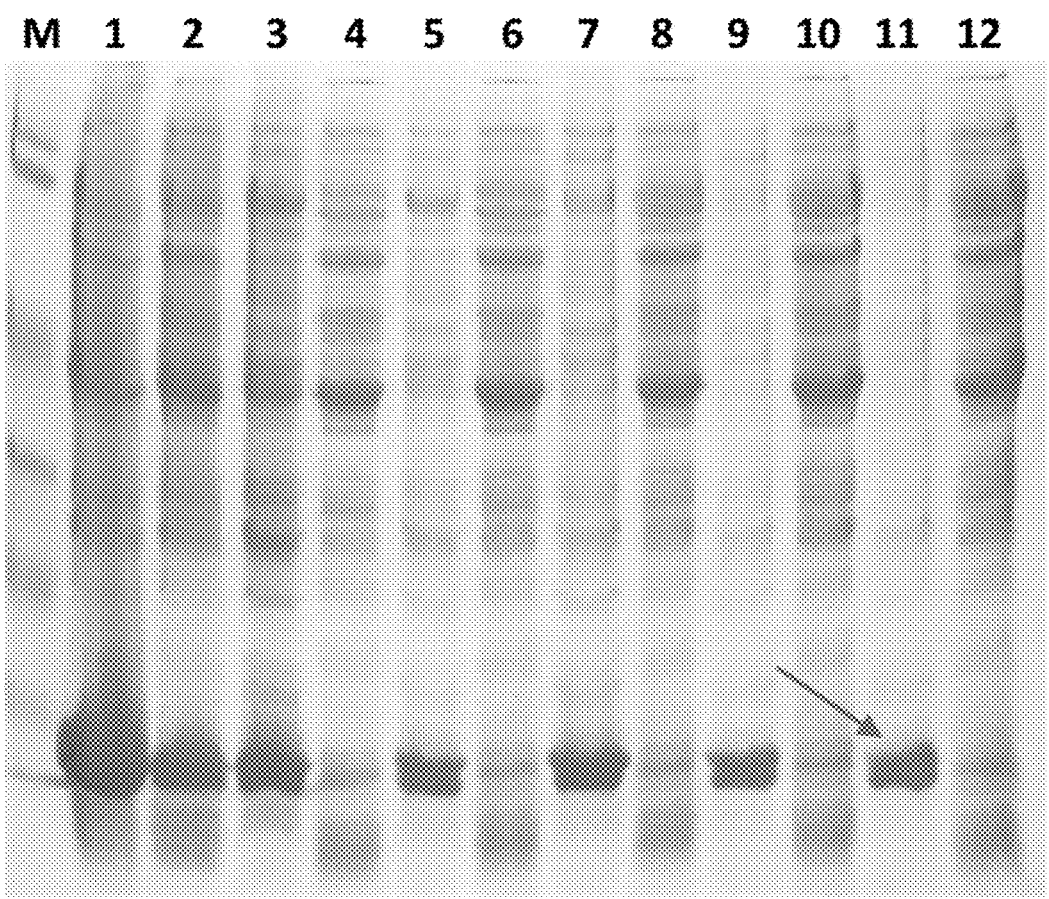
FIG. 3: SDS-PAGE analysis of precipitation of the fusion protein induced by temperature. 1: total intracellular protein; 2: soluble intracellular protein; 50° C. for 10 min, 3: pellet; 4: supernatant; 45° C. for 15 min, 5: pellet; 6: supernatant; 40° C. for 20 min, 7: pellet; 8: supernatant; 35° C. for 30 minutes, 9: pellet; 10: supernatant; 30° C. for 35 min, 11: pellet; 12: supernatant. In column 11, selective precipitation of the fusion protein with an approximate purity of 75% is observed.

The described SSD guide protein allows the chromatography step to be optional for the recovery of the fusion protein, giving the flexibility to choose between:
1) to recover in a single chromatography step the totality of the fusion protein produced, (FIG. 2 column 1); or
2) to recover only the fraction of fusion protein produced in insoluble form without the need for chromatography (FIG. 1A column 3);
3) to recover only the soluble fraction of the fusion protein, by means of a selective precipitation by incubation at a specific temperature, without the need of chromatography (FIG. 3, column 11).

These three forms are not obtainable using a guide protein known from the state of art. This is a technical result obtained due to the molecular properties of the SSD guide protein.

This method allows a gross intracellular productivity greater than 130 mg of peptide of interest per gram of dry cell, which corresponds to a substantial yield improvement. This improvement is not obtainable from the use of the guide proteins described in the state of art.

Up to 100 mg of peptide of interest is recovered per gram of dry cells, depending on the recovery method of the fusion protein used, which corresponds to an improvement in final productivity with respect to that described in the state of art.

The present invention allows an improvement in yield with respect to the prior art. The use of this SSD guide protein allows the evaluation of different recovery alternatives of the recombinant protein.

In addition to the obtaining of an increased productivity in expression and recovery of any recombinant peptide of interest, the method is carried out in a temperature range lower than that of previously described in the state of art.

APPLICATION EXAMPLES

Example

Step A: Constructing Expression Vector

An expression vector containing a coding sequence for the SSD guide protein of sequence SEQ ID NO: 1 was constructed. A sequence coding for a polyhistidine peptide at the N-terminus of the SSD guide protein and a coding sequence for a cutting site with thrombin at the C-terminal end were also incorporated. Finally, recognition sites were incorporated for the restriction enzymes AvrII and PacI, to be used as a cloning site of any nucleotide sequence coding for some peptide of interest. The design allows this last sequence to be inserted following the coding sequence for thrombin cleavage site. The DNA was incorporated into the expression vector pET22b (+) using the restriction sites recognized by the NdeI and XhoI enzymes, leaving the entire coding region under the control of the T7lac promoter.

The coding sequence for the peptide of interest p53pAnt was inserted into the expression vector containing the coding sequence for the SSD guide protein. For this, the nucleotide sequence encoding the p53pAnt peptide was synthesized as two pairs of complementary single-stranded oligonucleotides. The oligonucleotides were synthesized with the restriction sites for the AvrII and PacI enzymes, for cloning into the expression vector, in the reading frame of the guiding protein. This gene was digested, simultaneously with the expression vector, with the AvrII and PacI enzymes and then both fragments were ligated.

Step B: Inserting the Expression Vector into Host Cell

E. Coli BL21(DE3) cells were transformed with the ligation product, using resistance to ampicillin as selection marker.

Step C: Expressing the Fusion Protein

A culture of Escherichia coli cells transformed with the expression vector was grown in LB medium with 100 ug/mL of ampicillin for 15 hours and an inoculum for cell growth in fresh LB medium was used, with 100 μg/mL of ampicillin. The cells were grown up to an optical density of about 1.0 to 600 nm. Then, the IPTG inducer was added to a final concentration of 1 mM and cells were incubated at 25° C. for 3.5 hours. The cells were collected by centrifugation (5 min at 5,000×g) and the pellet was frozen at −20° C. for further methoding. In FIG. 1, it can be seen that the fusion protein is accumulated within the cell, reaching about 60% of the total intracellular protein (column 1).

Step D: Recovering the Fusion Protein

The recovery of the fusion protein was carried out using 3 different forms.

Recovery Form 1: Recovery of the Total Fusion Protein Expressed.

The Escherichia coli cells containing the fusion protein inside comprising the sequence of the SSD guide protein fused to the peptide sequence of interest were solubilized in 40 mM Tris solution, 500 mM NaCl, 8 M Urea, pH 8.0, and lysed by sonication. The solution was centrifuged 10 min at 10,000×g and the supernatant containing the fusion protein was collected. The fusion protein was purified by metal affinity chromatography using a nickel column. Using this method, it was possible to obtain 400 mg of fusion protein per gram of dry cell weight, with a purity greater than 95% in a single chromatographic step. In FIG. 2, column 1, the total protein recovered is shown.

Recovery Form 2: Partial Recovery of the Expressed Fusion Protein: Insoluble Fraction The *Escherichia coli* cells containing the fusion protein inside were solubilized in 40 mM Tris solution, 500 mM NaCl, pH 8.0, and lysed by sonication. The solution was centrifuged 10 min at 10,000×g and the pellet was collected, which was solubilized in 40 mM Tris, 500 mM NaCl, 8 M Urea, pH 8.0. The solubilized protein was centrifuged for 10 min at 10,000×g and the supernatant containing the fusion protein was recovered. By this method it was possible to obtain about 300 mg of fusion protein per gram of dry cell weight, with a purity greater than 90% without the need of purification by chromatography. In FIG. 1, column 3, the insoluble protein recovered is shown.

Recovery Form 3: Partial Recovery of the Expressed Fusion Protein: Soluble Fraction The *Escherichia coli* cells containing the fusion protein inside were solubilized in 40 mM Tris solution, 500 mM NaCl, pH 8.0, and lysed by sonication. The solution was centrifuged 10 min at 10,000×g and the supernatant was recovered. The fusion protein contained in the supernatant was recovered by selective precipitation by temperature. About 100 mg of fusion protein was obtained, with a purity of approximately 75%, by incubation at 30° C. for 35 minutes and without the need of purification by chromatography. In FIG. 3, column 11, the recovered soluble protein is shown.

Stage E: Cleaving the Fusion Protein

The peptide of interest was recovered from the fusion protein. For this, a cutting sequence between the SSD guide protein and the peptide of interest was previously introduced in the construction of the fusion protein.

The fusion protein was solubilized in cleavage solution 20 mM Tris, 150 mM NaCl, pH 8.0, 0.3% sarkosyl to be digested by thrombin protease. For this, the fusion protein recovered according to form 1 was dialyzed against cleavage solution; the fusion protein recovered according to form 2 was precipitated by dilution and then dissolved in cleaving solution; the fusion protein recovered according to form 3, was dissolved directly in cleavage solution. Enzymatic cleavage resulted in the digestion of up to 95% of the fusion protein.

Stage F: Purifying the Peptide of Interest

The peptide of interest released in the enzymatic cleavage was purified by metal affinity chromatography using a nickel column, recovering 80% of the free peptide.

In the case where the fusion protein was recovered in stage E, according to form 1, a final productivity of 100 mg of peptide per gram of dry cell weight was achieved; in the case where the fusion protein was recovered according to form 2, a final productivity of 55 mg of peptide per gram of dry cell weight was achieved; and in the case where the fusion protein was recovered according to form 3, a final productivity of 20 mg of peptide per gram of dry cell weight was achieved.

```
SEQUENCE LIST
SEQ ID NO 1: SSD guide protein:
DETGKELILVLYDYQEKSPRELTIKKGDILTLLNSTNKDWWKVEVND
RQGFFPAANLKKLD SEQ ID NO 2: Nucleotide sequence
GAT GAA ACC GGT AAA GAA CTT ATC CTG GTT CTG TAC

GAT TAT CAA GAG AAA AGC CCG CGC GAA TTG ACT ATT

AAG AAA GGC GAT ATT TTA ACC CTG CTC AAT TCT ACC

AAC AAG GAT TGG TGG AAA GTG GAA GTC AAC GAC CGT

CAG GGC TTC TTT CCA GCG GCC AAC CTG AAA AAA CTG

GAC
```

The invention claimed is:

1. An isolated peptide sequence of a guide protein for the production of a peptide of interest, comprising the sequence SEQ ID NO: 1.

2. An isolated peptide sequence of a guide protein for the production of a peptide of interest, comprising a sequence comprising at least 92% identity with SEQ ID NO: 1.

3. An isolated nucleotide sequence encoding the guide protein of claim 1, comprising the sequence SEQ ID NO: 2.

4. An expression vector of a fusion protein for the production of a peptide of interest, comprising:
   a sequence encoding for the guide protein, according to any of claim 1,
   (ii) a sequence that encodes a cleavage site, and
   (iii) at least one sequence encoding a peptide of interest, wherein the sequence which encodes the cleavage site is located between the sequences of (i) and (ii).

5. The expression vector of claim 4, further comprising a sequence encoding a purification tag.

6. The expression vector of claim 4, further comprising a sequence of an expression promoter operably linked to the sequence encoding the fusion protein.

7. The expression vector of claim 4, further comprising a sequence encoding at least one selection marker.

8. A host cell, transformed with the expression vector of claim 4.

9. The host cell of claim 8, selected from the group of microorganisms, consisting of *Escherichia coli*, *Bacillus subtilis*, and *Saccharomyces cerevisiae*.

10. A method for producing a peptide of interest, comprising:
    A) constructing an expression vector according to claim 4;
    B) inserting the expression vector of step A) into a host cell;
    C) expressing the fusion protein, culturing the host cell of step B) in a culture medium;
    D) recovering the fusion protein accumulated in the host cell;
    E) cleaving the fusion protein and
    F) purifying the peptide of interest.

11. The method of claim 10, wherein in step C) the host cell is cultured at a temperature between 20 and 40° C.

12. The method of claim 11, wherein in step C) the culture medium comprises a nutritive medium, a selection marker, and an inducer.

13. The method of claim 12, wherein the nutrient medium is Luria Bertani; the selection marker is ampicillin; and the inducer is isopropyl-β-D-1-thiogalactopyranoside.

14. The method of claim 10, wherein in step D) the separation and purification techniques are selected from centrifugation, chromatography, or precipitation.

15. The method of claim 10, wherein in step E) the fusion protein is solubilized in a cleavage solution by at least one step of dialysis, dilution, retention in column chromatography, or precipitation and dissolution.

16. The method of claim 15, wherein the cleavage solution is a semi-denaturing solution.

17. The method of claim 10, wherein in step E) the peptide is separated from the fusion protein by protease cleavage, chemical cleavage or metal-catalyzed cleavage.

18. The method of claim 10, wherein in step F) the peptide is purified by a chromatographic and/or precipitation method.

19. The method of claim 18, wherein the chromatographic method is selected from: metal affinity, size exclusion, or reverse phase.

20. An expression vector of a fusion protein for the production of a peptide of interest, comprising:
    (i) a sequence encoding for the guide protein, according to any of claim 2,
    (ii) a sequence that encodes a cleavage site, and
    (iii) at least one sequence encoding a peptide of interest, wherein the sequence which encodes the cleavage site is located between the sequences of (i) and (iii).

* * * * *

SEQUENCE LISTING

```
<160> NUMBER OF SEQ ID NOS: 2

<210> SEQ ID NO 1
<211> LENGTH: 61
<212> TYPE: PRT
<213> ORGANISM: Artificial Sequence
<220> FEATURE:
<223> OTHER INFORMATION: guide protein SSD

<400> SEQUENCE: 1

Asp Glu Thr Gly Lys Glu Leu Ile Leu Val Leu Tyr Asp Tyr Gln Glu
1               5                   10                  15

Lys Ser Pro Arg Glu Leu Thr Ile Lys Lys Gly Asp Ile Leu Thr Leu
            20                  25                  30

Leu Asn Ser Thr Asn Lys Asp Trp Trp Lys Val Glu Val Asn Asp Arg
        35                  40                  45

Gln Gly Phe Phe Pro Ala Ala Asn Leu Lys Lys Leu Asp
    50                  55                  60

<210> SEQ ID NO 2
<211> LENGTH: 183
<212> TYPE: DNA
<213> ORGANISM: Artificial Sequence
<220> FEATURE:
<223> OTHER INFORMATION: nucleotide sequence of guide protein SEQ ID
      NO: 1
```

```
<400> SEQUENCE: 2
gatgaaaccg gtaaagaact tatcctggtt ctgtacgatt atcaagagaa aagcccgcgc      60
gaattgacta ttaagaaagg cgatatttta accctgctca attctaccaa caaggattgg     120
tggaaagtgg aagtcaacga ccgtcagggc ttctttccag cggccaacct gaaaaaactg     180
gac                                                                   183
```